US011497459B2

(12) United States Patent
Jackson et al.

(10) Patent No.: US 11,497,459 B2
(45) Date of Patent: Nov. 15, 2022

(54) METHODS AND SYSTEM FOR OPTIMIZING AN IMAGING SCAN BASED ON A PRIOR SCAN (71) Applicant: General Electric Company, Schenectady, NY (US)

(72) Inventors: John Irvin Jackson, Brookfield, WI (US); Dominic Joseph Crotty, Waukesha, WI (US); Franco Rupcich, Wauwatosa, WI (US); John Londt, Oconomowoc, WI (US); Mark Vincent Profio, Elm Grove, WI (US); Darin Robert Okerlund, Muskego, WI (US)

(73) Assignee: General Electric Company, Schenectady, NY (US)

(*) Notice: Subject to any disclaimer, the term of this patent is extended or adjusted under 35 U.S.C. 154(b) by 531 days.

(21) Appl. No.: 15/881,402

(22) Filed: Jan. 26, 2018

(65) Prior Publication Data

US 2019/0231296 A1 Aug. 1, 2019

(51) Int. Cl.
*A61B 6/00* (2006.01)
*G06T 11/00* (2006.01)
*A61B 6/03* (2006.01)

(52) U.S. Cl.
CPC ............. *A61B 6/542* (2013.01); *A61B 6/032* (2013.01); *G06T 11/005* (2013.01); *G06T 2207/10081* (2013.01)

(58) Field of Classification Search
CPC ......... A61B 6/06; A61B 6/4035; A61B 6/405; A61B 6/542; A61B 6/4233; A61B 6/4241; A61B 6/4266; A61B 6/4275; A61B 6/025; A61B 6/03; G01N 23/046; G03G 15/0545
See application file for complete search history.

(56) References Cited

U.S. PATENT DOCUMENTS

| | | | | |
|---|---|---|---|---|
| 2004/0032928 | A1* | 2/2004 | Toth | A61B 6/032 378/108 |
| 2006/0064396 | A1* | 3/2006 | Wei | A61B 6/463 |
| 2009/0262885 | A1* | 10/2009 | Bontus | A61B 6/027 378/11 |
| 2013/0101079 | A1* | 4/2013 | Hough | A61B 6/545 378/8 |
| 2013/0116554 | A1* | 5/2013 | Kaiser | A61B 6/40 600/425 |
| 2014/0270452 | A1* | 9/2014 | Goshen | G06T 3/4053 382/131 |
| 2015/0164457 | A1 | 6/2015 | Nett et al. | |
| 2016/0106387 | A1* | 4/2016 | Kahn | A61B 6/5211 378/62 |
| 2016/0206256 | A1* | 7/2016 | Berglund | A61B 6/4233 |
| 2016/0242712 | A1* | 8/2016 | Jin | A61B 6/488 |

(Continued)

*Primary Examiner* — David P Porta
*Assistant Examiner* — Mamadou Faye (57) ABSTRACT

Methods and systems are provided for adjusting medical imaging parameters based on imaging parameters used during a previous imaging session. In one embodiment, a method for a computed tomography (CT) system includes reducing a radiation level of at least one CT scan of one or more successive CT scans performed on a patient based on CT scan information obtained from a previous CT scan performed on the patient, the radiation level reduced relative to a radiation level of the previous CT scan.

20 Claims, 3 Drawing Sheets

(56) References Cited

U.S. PATENT DOCUMENTS

| | | | |
|---|---|---|---|
| 2016/0253443 A1* | 9/2016 | Li | G06T 7/0002 |
| | | | 703/2 |
| 2017/0135659 A1* | 5/2017 | Wang | G06T 11/005 |
| 2019/0133544 A1* | 5/2019 | Liu | A61B 5/72 |

\* cited by examiner

METHODS AND SYSTEM FOR OPTIMIZING AN IMAGING SCAN BASED ON A PRIOR SCAN

FIELD

Embodiments of the subject matter disclosed herein relate to medical imaging, and more particularly, to configuring imaging parameters for an imaging session based on a previous imaging session.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a method for a computed tomography (CT) system includes reducing a radiation level of at least one CT scan of one or more successive CT scans performed on a patient based on CT scan information obtained from a previous CT scan performed on the patient, the radiation level reduced relative to a radiation level of the previous CT scan. In this way, CT scan information from a previous CT scan of the patient may be used to scale scanning parameters of a subsequent CT scan in a manner that lowers the radiation dose the patient is exposed to. In one example, the scanning parameters may be scaled to lower the radiation level while also maintaining an acceptable level of image quality for the images reconstructed from the data acquired during the subsequent CT scan, so that a diagnostic clinical goal may be met. By lowering the radiation level for at least one of the one or more successive CT scans, the risks associated with multiple CT scans performed on the same patient may be lowered.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of configuring imaging parameters for a computed tomography (CT) system. During a CT system imaging session, a subject is imaged using x-ray measurements taken from different angles to produce cross-sectional (tomographic) images of specific areas of the scanned subject. CT imaging is useful in a variety of medical applications, including diagnosis and monitoring of lesions. As such, a patient may undergo multiple CT imaging sessions over a period of time, such as during oncology treatment, in order to monitor the growth or shrinkage of a lesion, for example. While a CT system provides a non-invasive mechanism to monitor progress of a treatment, for example, repeated exposure to the doses of radiation may be undesirable. During a typical series of CT imaging sessions, the same imaging parameters, including the same dose of radiation, may be applied during each imaging session, as the imaging parameters are frequently based on the target anatomy being imaged. However, such a configuration may result in the patient being exposed to more radiation than necessary to monitor the change in lesion size, for example.

Thus, according to embodiments disclosed herein, imaging parameters from a prior imaging session may be used to modulate current imaging parameters in order to image a subject using a lowest possible dose of radiation while still maintaining an acceptable level of image quality. For example, an initial imaging session may be conducted using default imaging parameters based on target scanned anatomy that results in relatively high imaging quality. Then, subsequent imaging sessions may be conducted where the imaging parameters used during the initial imaging session are scaled in order to reduce radiation dose. The scaling of the imaging parameters may be based on clinical goal of the imaging session whereby an acceptable level of quality of the images are defined. Further, if the body mass of the imaged subject changes over the course of the treatment, the imaging parameters may be updated to maintain an appropriate dose of radiation.

Though a CT system is described by way of example, it should be understood that the present techniques may also be useful when applied to other imaging modalities, such as positron emission tomography (PET), magnetic resonance imaging (MRI), ultrasound, and so forth. The present discussion of a CT imaging modality is provided as an example of one suitable imaging modality.

Figure 1:
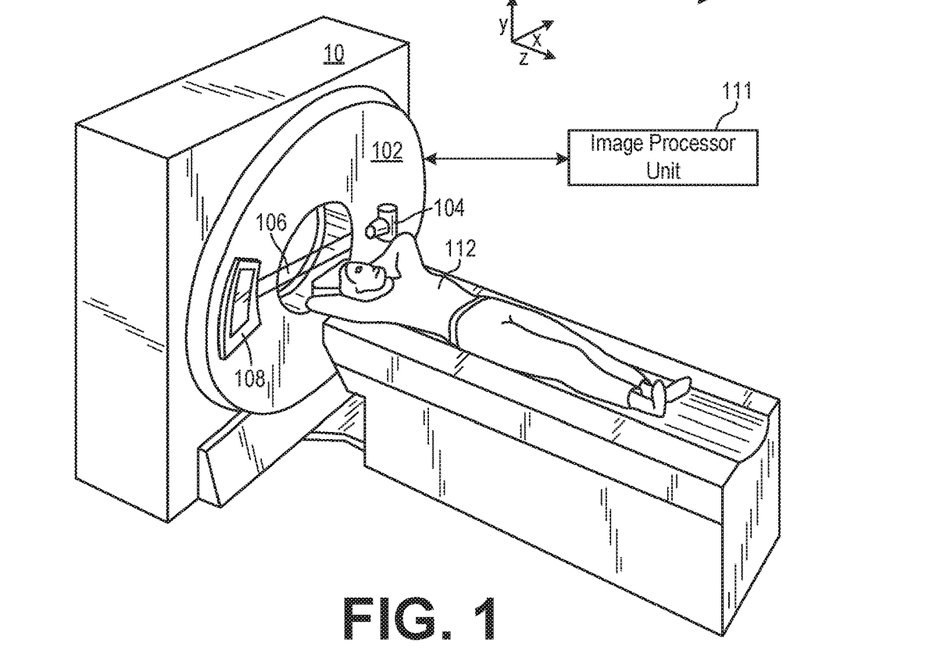
FIG. 1 shows a pictorial view of an example imaging system.

FIG. 1 illustrates an exemplary CT system 100. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a stationary housing 10 that houses a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources may be employed to project a plurality of x-rays 106 for acquiring projection data corresponding to the subject 112 at different energy levels.

In certain embodiments, the CT system 100 further includes an image processor unit 111 configured to reconstruct images of a target volume of the subject 112 using an iterative or analytic image reconstruction method. For example, the image processor unit 111 may use an analytic image reconstruction approach such as filtered backprojection (FBP) to reconstruct images of a target volume of the patient. As another example, the image processor unit 111 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection (FBP) technique. Transmission and emission tomography reconstruction techniques also include statistical iterative methods such as maximum likelihood expectation maximization (MLEM) and ordered-subsets expectation reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

Figure 2:
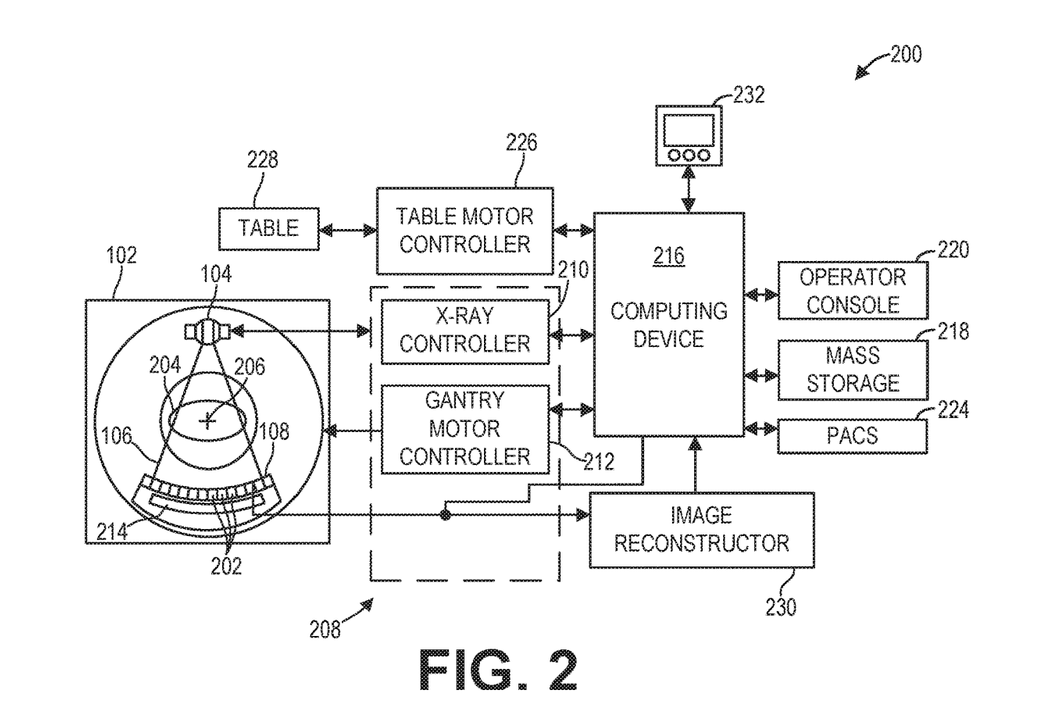
FIG. 2 shows a block schematic diagram of an example imaging system.

FIG. 2 illustrates an exemplary imaging system 200 similar to the CT system 100 of FIG. 1. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray radiation source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device such as mass storage 218. The mass storage 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) and/or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more of the functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device or mass storage 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. For example, image reconstructor 230 may include such executable instructions in non-transitory memory, and may apply the instructions to reconstruct an image from scanning data. Computing device 216 may include instructions in non-transitory memory, and may apply the methods described herein, at least in part, to optimize scan and reconstruction parameters. In yet another embodiment, the methods and processes described herein may be distributed across computing device 216 and other computing devices, such as a remote computing device.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
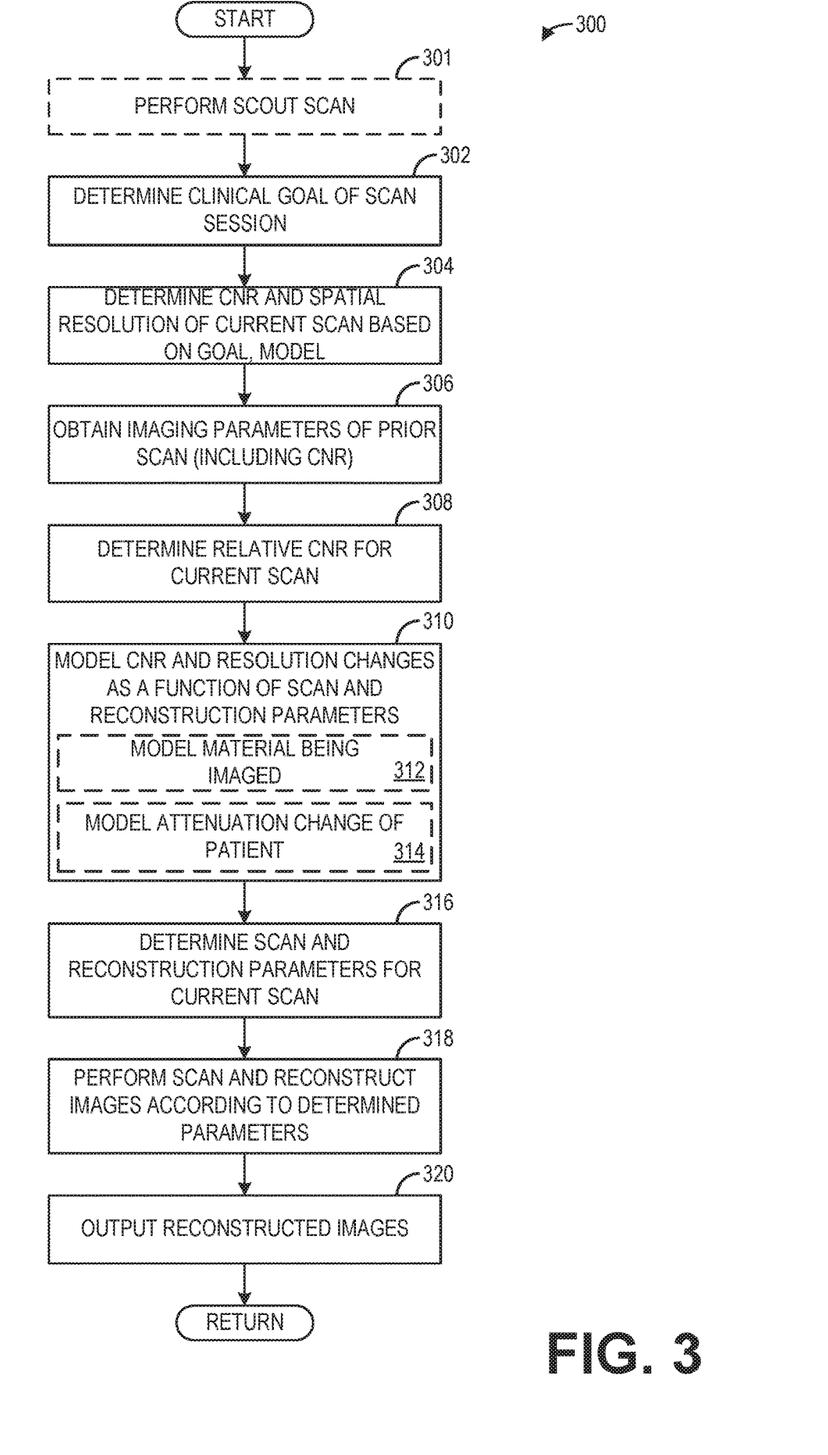
FIG. 3 is a flow chart illustrating a method for operating a CT imaging system.

Turning to FIG. 3, a method 300 for operating a CT system is shown. Method 300 is described with regard to the systems and components depicted in FIGS. 1 and 2, though it should be appreciated that the method may be implemented with other systems and/or components without departing from the scope of the present disclosure. Method 300 may be implemented as executable instructions in non-transitory memory of a computing device, such as computing device 216.

Method 300 may be executed to optimize scan parameters used to perform a CT scan and/or reconstruction parameters used to reconstruct an image from projection data obtained during the CT scan. As explained above, some patients may undergo repeated CT exams to determine changes in a condition over time. For example, an oncologist may want to know if a tumor is growing, or if a therapy is being effective in reducing the size of a tumor. Thus, a patient may have one or more CT exams after an initial exam, where the size or shape of an object (such as a lesion) is compared with that object at a previous time. Because the location, contrast level difference, and preliminary shape of the object are already known from the initial scan, the subsequent scan may be performed using scan parameters that allow for a radiation dose level that may be significantly lower than radiation dose level during the initial scan, and yet be fully sufficient to answer the clinical question of the change in the object over time; otherwise, the imaging technique may have a higher dose than the minimum required to reliably make the diagnostic decision.

At 301, method 300 optionally includes performing a scout scan on a patient. A scout scan may include fixing the position of the x-ray source and translating the patient in a z-axis direction. Projection data acquired during the scout scan may be used to generate a scout image that is similar to a plain radiography image. Using the scout image, an operator may identify anatomical landmarks to ensure the target anatomy is in the field of view and so that proper techniques may be selected for different areas of the patient. However, the scout scan may be optional and other techniques for ensuring the patient is positioned properly with the target anatomy in the field of view may be performed instead. If a scout scan is performed, attenuation data of the patient may be determined and stored in memory of the computing device.

At 302, method 300 includes determining a clinical goal of the current imaging session. The clinical goal may be determined based on user input. For example, an operator of the imaging system (e.g., a clinician or technician) may input a clinical goal via a user interface. In other examples, the clinical goal may be determined based on a pre-defined treatment protocol for the patient. The clinical goal may include measurement of a change in size or position of a target anatomical feature, such as a clinical goal to generate images of a patient who had a prior tumor of size X (based on measurements taken during a prior scan), to see if the tumor has changed in size by more than a threshold amount, such as 10%. In another example, the clinical goal may include more specific imaging parameters, such as a clinical goal to generate an image with a contrast to noise ratio (CNR) of C at a particular location/target anatomy, with the resolution provided by a slice thickness of S and reconstruction kernel K.

In an example, determining the clinical goal may include receiving a selection of an imaging protocol. An operator of the imaging system may select, via a user interface of the imaging system, an imaging protocol that specifies the anatomy and clinical goal of the exam. The imaging protocol may comprise an indication of a task (such as detection, screening, and so on) for the exam. The imaging protocol may further comprise an indication of a targeted contrast level, a targeted lesion size, critical to quality (CTQ) parameters, and so on. For example, a first imaging protocol may include CTQs that indicate spatial resolution is to be prioritized, while a second imaging protocol may include CTQs that indicate image quality is to be prioritized. For some screening tasks, for example, a corresponding imaging protocol may include CTQs that indicate dose is important. Other CTQs that may be prioritized include x-ray dose target, temporal resolution, contrast to noise ratio, signal to noise ratio, and low contrast detectability.

At 304, method 300 includes determining a target CNR and spatial resolution for the current scan based on the clinical goal and a model. For example, when the clinical goal includes determining if a tumor has changed in size by more than 10%, a maximum tolerated measurement error may be determined based on simulations or experiments, where the maximum tolerated measurement error is associated with measuring a distance, area, or volume of a roughly ellipsoidal shape with a relative CNR of C and resolution R. Multiple paired values of (C, R) may be generated that will each fulfill the clinical goal, as it may be possible to achieve clinical goal (e.g., of measuring the size of the tumor) without exceeding the maximum tolerated measurement error with multiple CNRs by varying the target resolution. The model may be generated by measuring the size of various-sized objects with various CNRs, and then computing the standard deviation of the measurements for each of the contrast and noise levels. Automated measurement tools may also be used, performing repeated measurements on simulated images while varying the noise.

At 306, method 300 includes obtaining imaging parameters of one or more images generated during a prior scan performed on the same patient. The imaging parameters may include scan parameters (e.g., settings of the CT system during the scan, such as x-ray tube current, x-ray tube voltage, and filter type or shape), reconstruction parameters (e.g., reconstruction kernel), and/or image quality parameters (e.g., CNR). For example, the CNR of a prior image obtained in a prior scan may be measured, such as by measuring a first average CT number in a first region of interest, such as a tumor, and a second CT number in a second region of interest, such as the tissue just outside of the tumor, subtracting the second CT number from the first CT number, and dividing by a measurement of the standard deviation of the image in that region. The location of the regions may be important, as the noise level may not be constant across the image or volume. The measurement may be manually done by a technologist, or done using an automated algorithm. The measurement may be stored in the computing device executing method 300 and/or obtained from a remote computing device. The prior image(s) may be generated during a prior scan session that is temporally separate from the current scan and may include images taken during a diagnostic scan mode rather than a scout scan mode. As mentioned above, a scout scan is typically performed without rotating the gantry and thus does not generate depth information. Further, the scout scan may be performed at a lower radiation dose and/or with other scan parameters that result in relatively low resolution or low quality images. Thus, the scan parameters used to generate the prior image(s) may not be the scan parameters used in a scout scan.

At 308, method 300 includes determining a relative CNR for the current scan based on the measured CNR of the prior image and the target CNR determined at 304. For example, the relative CNR may be determined by dividing the target CNR by the measured CNR from the prior image. At 310, method 300 includes modeling changes in CNR and scan resolution as a function of scan and reconstruction parameters. For example, based on simulations or experimental scans, the noise level and resolution changes with various scan and reconstruction settings may be measured. Example scanning settings that may be adjusted (and the resultant CNR and resolution changes modeled) may include the kVp level (or dual energy), mAs (mA and exposure duration at each location), bowtie filter (which may have a small or larger effect depending on the location of the region of interest), standard or high resolution imaging mode, and/or focal spot size. Example reconstruction settings that may be adjusted (and the resultant CNR and resolution changes modeled) may include the reconstruction kernel, adaptive statistical iterative reconstruction (ASiR) level, slice thickness, pixel size, and/or reconstructed/displayed field-of-view (DFOV).

For example, noise changes roughly as the square root of the mAs. Thus, the CNR may be scaled by scaling the mAs. In another example, if the region of interest, such as the tumor, has a different chemical makeup than the neighboring tissues, then the contrast of the region of interest may change as a function of the kVp, and this change may be modeled. For example, regions with iodine, such as in an injected contrast agent, show an increased contrast at lower kVp levels.

In some examples, as indicated at 312, the material composition of the material being imaged may be modeled. The material being scanned may be noted and incorporated into the optimization. For example, if the region being scanned includes more iodine than neighboring regions, then a lower kVp will increase the level of image contrast. Further, in some examples, as indicated at 314, the attenuation change of the patient being scanned may be modeled. This allows for a change in the patient's size (e.g., since the prior scan) to be accounted for when selecting optimal scan and reconstruction settings. For example, patients undergoing cancer treatment may have significant increases or decreases in body attenuation. An estimated change in attenuation may be based on a change in the patient's weight, or based on the relative x-ray attenuation of the scout images of the current and the prior scanning session. This change in patient attenuation may be incorporated into the calculation of the scan parameters. For example, if the patient's attenuation has increased by P, and an increase in P is known or estimated to increase noise by f(P), then these values may be incorporated into the determination of the imaging parameters for the current scan, as will be discussed below.

At 316, method 300 includes determining scan and reconstruction parameters for the current scan. The scan and reconstruction parameters that are to be applied during the current scan may be determined based on the target CNR and resolution described above, as well as the modeling of the CNR and resolution changes. For example, the scan and reconstruction parameters from the previous scan may be scaled in such a way that the CNR and resolution targets are met. The CNR and resolution targets may be met with more than one set of scan parameters, and thus the set of scan parameters that meet a predetermined scanning priority may be selected, such as the parameters that minimize radiation dose to the patient or parameters that maintain image quality. As explained above, the imaging protocol and/or clinical goal of the scanning session may dictate whether a low dose of radiation is to be prioritized, high image quality is to be prioritized, or other factor is to be prioritized. The set of scan and reconstruction parameters that achieves this priority may be selected.

For example, the effects of adjusting the scan and/or reconstruction parameters on the CNR and spatial resolution may be modeled for each of a plurality of different sets of scan and/or reconstruction parameters. The sets of scan and/or reconstruction parameters that achieve the target CNR and spatial resolution may be identified. Then, the radiation level that would be output by the x-ray radiation source of the CT system during the current scan for each of the identified sets of scan and/or reconstruction parameters may be calculated (e.g., based on the mAs, kVp, filter shape, helical scan pitch, slice thickness/number, scanner geometry, and/or current modulation scheme). For example, a measure of expected contrast may be associated with each kVp for soft tissue and for regions containing iodinated contrast agent. A measure of resolution may be associated with each reconstruction kernel, based on a modulation transfer function (MTF) measurement at a particular level, such as the MTF 10% value. A measure of the relative noise level, as measured by the standard deviation within a small region of interest (ROI) within a homogenous region of tissue, may be estimated based on the relative noise measured within a water phantom for each of the reconstruction kernels that are available on the system. The relative CNR is the inverse of the relative noise level. Note that some reconstruction kernels are only available with certain acquisition scan modes, such as those that do or do not wobble the x-ray source on the anode, commonly known as high resolution or standard acquisition modes. The slice thickness of the reconstructed images can also be varied, such as from 0.625 mm to 1.25 mm, with an associated 50% reduction in spatial resolution in the z-direction, and a reduction in noise level by approximately 29% (1−sqrt(2)/2), corresponding to an increase in CNR of 29%. Advanced iterative reconstruction can also be used to reduce the noise level, or to allow equal noise level with a reduced mAs, by an amount estimated from prior experimental phantom or clinical image measurements. The set that results in the lowest radiation level may then be selected.

At 318, the method includes performing a diagnostic scan and reconstructing one or more images according to the determined scan and reconstruction parameters. During the diagnostic scan, the imaging source (e.g., x-ray projector) is activated according to the specified scan parameters (e.g., at a specified kV, mA, attenuation filter position) and the rotation of the gantry is controlled to achieve the scan angles specified by the imaging protocol. Further, during the scan, the position of the table may be moved such that the scan progresses from a start scan location to a stop scan location. The image(s) are reconstructed based on data acquired during the scan. The one or more images may be reconstructed using, as a non-limiting example, an analytic reconstruction algorithm, such as filtered backprojection or an iterative reconstruction algorithm, as dictated by the determined reconstruction parameters. At 320, the method includes outputting the reconstructed image(s). For example, the one or more images may be output to a display device, such as display 232 of FIG. 2. In this way, the operator of the imaging system may review the image(s). Method 300 then ends.

Thus, method 300 provides for obtaining the scan and reconstruction parameters used to generate a prior image of a patient as well as image quality parameters of the prior image and then determining scan and reconstruction parameters for a current scan based on these prior scan and reconstruction parameters. The prior scan may be performed on the same CT scanner/imaging system model as the current scan, or the prior scan may be performed with a different CT scanner model. Differences in scanner parameters and their impact on image contrast, noise, resolution, and other parameters may be incorporated in the model described above. Further, other metrics (for example, other than CNR) or measurements or models or modeling methods may be used, while maintaining the goal of using a prior image and its associated imaging technique to influence the imaging technique of a subsequent exam.

The method includes determining a target spatial resolution, noise level, and/or contrast to noise ratio for a current CT imaging session based on a clinical goal. The clinical goal may be defined by a clinician, for example. The clinical goal may include a maximum tolerated measurement error, if the clinical goal includes measuring the size of a region of interest, such as tumor. The clinical goal may include specific imaging parameters, such as contrast to noise ratio. The scan parameters used to generate an image of the same region of interest of the same patient during a prior scanning session are obtained. The scan parameters may include the kVp, mA, and attenuation filter. These scan parameters may be scaled until the scan parameters that result in a lowest dose of radiation are identified, that still achieve the target spatial resolution, noise level, and/or contrast to noise ratio. A similar process may optionally be performed with the reconstruction parameters (e.g., kernel, slice thickness, pixel size). In this way, certain image parameters, such as resolution or quality, may be reduced in order to lower the dose of radiation to which the patient is exposed, while still generating images of sufficient resolution, quality, etc., to allow the clinical goal to be achieved.

Oncology patients may lose weight over the course of an oncology treatment. As explained above, it may be desirable to account for the change in weight during scanning. For example, if patient weight has changed, but the clinical goal and/or imaging protocol dictates that the signal to noise ratio (SNR) of the prior image be maintained in a current image, the mA may be scaled by a function of the absolute or relative change in weight, or based on the ratio of the current projection data to the prior projection data. In another example, the clinical goal and/or imaging protocol may dictate that the kV be the same across the scanning sessions to maintain the same contrast between various anatomical regions. If multiple follow-up scans will be performed, scans 2 through N (e.g., all follow up scans subsequent to the initial scan) may be at a different kV than the initial scan. Alternatively, all may be at the same kVp.

The approach described herein may be used in multiple scenarios to allow the scan and reconstruction parameters of a prior image of a patient to be used to configure scan and reconstruction parameters for a current image of the patient. For example, the computing device may include a tool that takes a prior scan and determines a scan protocol that would match a desired image, based on the parameters of the prior scan. In examples where the prior scan was a GSI scan (dual energy) that generated a GSI image, the GSI image parameters may be used to determine the best single kVp for a subsequent scan. In an example, the initial scan (e.g., scan T0) may be conducted with one set of settings. Using the approach described herein, the subsequent scan (e.g., scan T1) may be optimized so that follow-up images T1 through TN are as similar as possible (same kVp), but may have different dose/mA to keep the noise consistent. In addition to optimizing the settings of the CT scanner, the approach allows for the optimization of the kernel, ASiR level, and/or standard or high-resolution mode, to give resolution and CNR sufficient for the clinical goal. Further, rather than use noise as a metric, other measures other than noise (local standard deviation in a uniform area) may be used, such as the noise at a particular spatial frequency (using the noise power spectrum), or fractal dimension (peak spatial frequency), which may be normalized to the pixel size.

In any of the examples presented above, the result is that the radiation dose for a patient's follow-up exam is sufficient for achieving the clinical goal but does not excessively exceed or under-deliver what is needed for the subsequent exam. Furthermore, a series of follow-up exams can all be dose-optimized to allow for tracking of changes within a required statistical accuracy, or can be designed to maintain consistent image quality, despite the significant changes in patient's mass that can occur during treatment.

Figure 4:
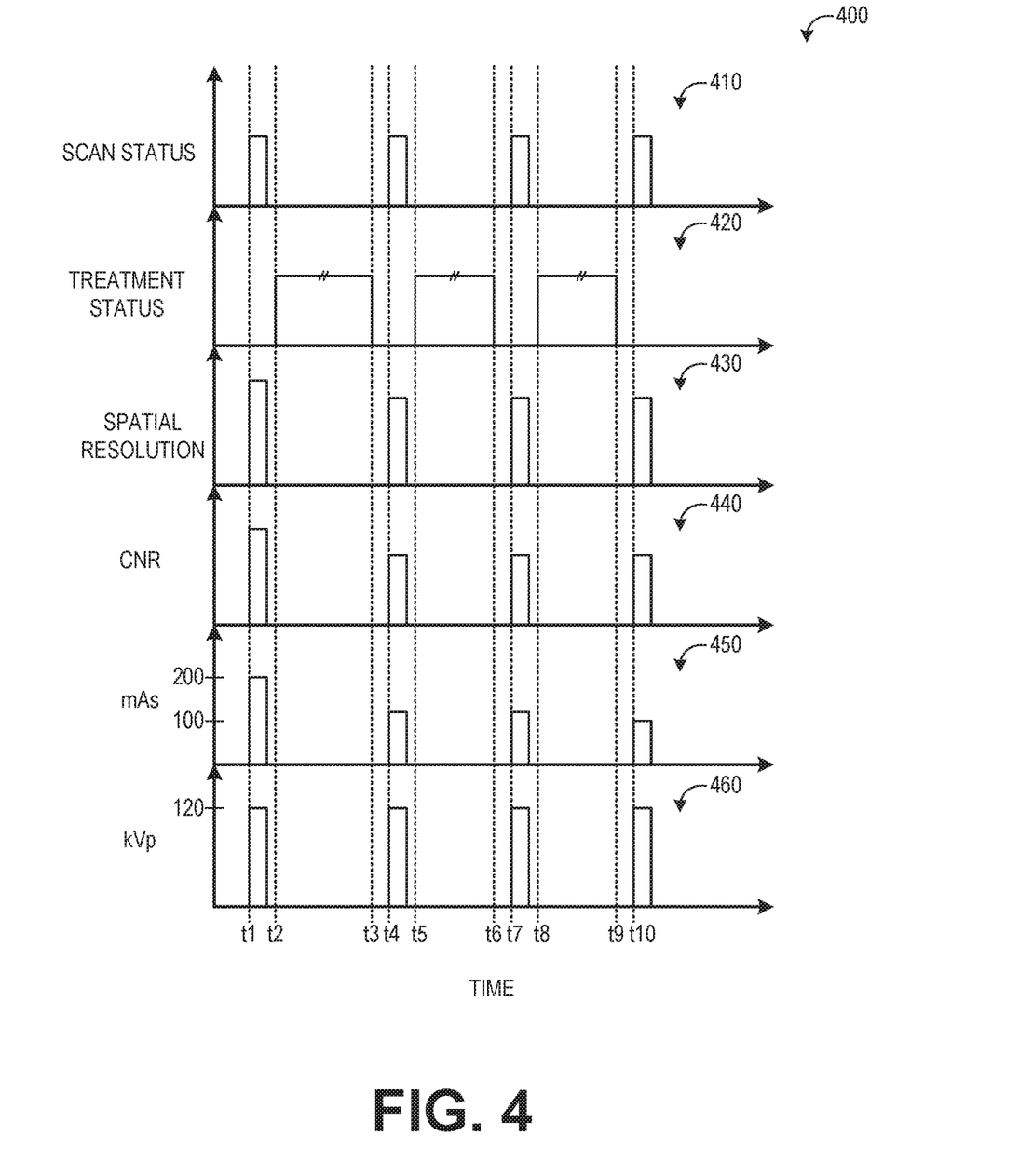
FIG. 4 is a timeline showing scan parameters over a series of successive CT scans.

FIG. 4 shows a timeline 400 of scan parameters during a series of CT scans performed on the same patient, according to embodiments disclosed herein. The first plot from the top, plot 410, illustrates CT scan status. A bar represents that a CT scan on the patient is being performed. The second plot of the top, plot 420, illustrates treatment status. The rectangles represent that treatment for a condition being monitored by the CT scans is being performed. In one example, the condition may include the patient having a tumor, and the treatment may include chemotherapy to reduce the size of the tumor. The third plot from the top, plot 430, illustrates spatial resolution for an image acquired during a respective CT scan. The fourth plot, plot 440, represents contrast to noise ratio (CNR) for the image acquired during the respective CT scan. The fifth plot, plot 450, represents the effective x-ray tube current (mAs) output by the CT system during the respective CT scan. The sixth plot, plot 460, represents the peak x-ray tube voltage output by the CT system during the respective CT scan. Time is depicted along the horizontal axis (x-axis). Respective values for each scan parameters are depicted along the vertical, y-axis. The scan status and treatment status plots are binary, indicating only whether or not a CT scan or treatment is occurring. The plots are all time-aligned. It is to be understood that the treatment may have a duration that is longer than that shown in FIG. 4, as represented by the hatch marks in the treatment status plot. Further, in some examples, the treatment may be performed continuously, even during the CT scans, such as when the treatment includes daily administration of an oncology drug.

An initial CT scan is performed at time t1, prior to initiation of the course of treatment. The initial CT scan may be used to diagnose the presence, size, location, and/or other properties of the tumor, for example. The initial CT scan may be performed with default scan and reconstruction parameters that are based on the anatomical region being imaged (e.g., the abdominal region) and the diagnostic goal (e.g., identifying the tumor). As such, image quality may be prioritized, including relatively high spatial resolution and CNR. The initial CT scan may be performed with x-ray tube current of 200 mAs and the x-ray tube voltage of 120 kVp. Such values are exemplary and other values are possible.

At time t2, after the initial CT scan, a first round of treatment commences and has a suitable duration depending the on the treatment. As shown, the first round of treatment commences at time t3. At a time following commencement of the treatment, herein shown at time t4, a first CT scan following the initial CT scan is performed. The first CT scan may be temporally spaced apart from the initial CT scan and may be separated by the first round of treatment. The first CT scan may be performed a suitable time after the initial CT scan, such as one week or one month after the initial CT scan.

The first CT scan (performed at time t4) may be performed in order to monitor the size of the tumor identified in the initial CT scan. An operator of the CT system may input a clinical goal for the first CT scan to the CT system. The clinical goal may include the initial size of the tumor (e.g., between 9.9 and 10.1 cc in volume), an indicated change in size to be detected (has the tumor grown or shrunk by at least 10%), and a confidence level (e.g., 99%). From this, a measurement error may be calculated as part of the clinical goal. As an example, the measurement error may be calculated by determining the threshold measured change in size of the tumor (the change in size of the tumor that would result in the tumor growing or shrinking by 10%), and then dividing by a standard deviation that corresponds to a 99% confidence level, in this example $(11-10.1)/2.575=0.35$ cc. The measurement error may be used to determine a target CNR and target spatial resolution for the first CT scan, according to a model as explained above with respect to FIG. 3.

In the example shown in FIG. 4, the CNR and spatial resolution for the first CT scan may each be lower than the CNR and the spatial resolution of the initial CT scan. In some examples, the model may output more than one target CNR and target spatial resolution, since it may possible to achieve the determined measurement error with multiple CNRs by varying the spatial resolution. The target CNR and/or spatial resolution that is selected for the first CT scan may be selected based on modeling the impact of the available scan and reconstruction parameters and combinations thereof on the CNR and spatial resolution, and then selecting the set based on this modeling using additional criteria, such as selecting the set that has the lowest radiation.

Because the target CNR and resolution are lower compared to the CNR and spatial resolution of the initial scan, the x-ray source energy output may be lowered as well. In the example presented in FIG. 4, the clinician may determine that the contrast is to be maintained in the first CT scan to aid in visualizing the tumor. Thus, the x-ray tube voltage is kept at 120 kVp and the effective x-ray tube current is scaled in order to meet the target CNR and resolution without delivering excess radiation. Thus, the x-ray tube current is lowered to 125 mAs for the first CT scan.

After the first CT scan, a second round of treatment commences at time t5 and ends at time t6. At time t7, a second CT scan is performed on the patient. The second CT scan may be performed with the same scan parameters as the first CT scan, as the tumor may not have changed in size appreciably and the patient may be of the relatively same weight. After the second CT scan, a third round of treatment is performed from time t8 to time t9. At time t10, a third CT scan is performed on the patient. At the time of the third CT scan, the patient may have lost weight, relative to the weight of the patient at the initial scan. Thus, the third CT scan may be performed with the same voltage (120 kVp), but with even lower current (such as 100 mAs). By doing so, the target CNR and spatial resolution may still be achieved, but with less radiation since the attenuation of the body of the patient has changed due to the patient losing weight.

In this way, a radiation level of at least one CT scan of one or more successive CT scans performed on a patient may be reduced based on CT scan information obtained from a previous CT scan performed on the patient, the radiation level reduced relative to a radiation level of the previous CT scan. For example, the previous CT scan may be an initial CT scan, such as a CT scan performed to initially locate and size a lesion. Each of the one or more successive CT scans may be performed after the initial CT scan, and each of the one or more successive CT scans is temporally spaced apart from a prior CT scan (e.g., the CT scan performed immediately prior the current CT scan) by a treatment period during which the patient undergoes treatment for a condition monitored by the one or more successive CT scans (e.g., an oncology treatment). The initial CT scan may be performed with the CT system configured with a first set of scan parameters. The first set of scan parameters may be selected (e.g., semi-automatically by the CT system) based on an anatomical region of interest being scanned in the initial CT scan (which may be indicated from user input, for example).

In an example, the at least one CT scan may include a first CT scan following the initial CT scan. Thus, the radiation level of the first CT scan may be reduced based on CT scan information obtained from the initial CT scan by scaling at least one scan parameter of the first set of scan parameters to generate a second set of scan parameters. The first CT scan may then be performed with the CT system configured with the second set of scan parameters to reduce the radiation level. The scan parameter(s) may include one or more of an x-ray tube current, an x-ray tube voltage, filter type or shape, imaging resolution mode, and focal spot size. In an example, the at least one scan parameter may be scaled by an amount based on a target contrast to noise ratio and/or target spatial resolution for the first CT scan, such as by an amount to achieve a lowest possible radiation level while also maintaining a contrast to noise ratio of the first CT scan at or above the target contrast to noise ratio and/or while also maintaining a spatial resolution of the first CT scan at or above the target spatial resolution. Further, in some examples, a change in attenuation of the patient relative to the initial CT scan may be determined and the radiation level may be reduced by scaling an x-ray tube current of the CT system during the first CT scan based on the change in attenuation.

In an example, the target contrast to noise ratio and/or target spatial resolution may be determined based on a clinical goal of the first CT scan and image information taken from one or more images reconstructed from data acquired during the initial CT scan. The image information may include information usable to identify a size of a lesion of the patient, and the clinical goal may include measuring the size of the lesion at each of the one or more successive CT scans with a maximum measurement error tolerance. The target contrast to noise ratio and/or target spatial resolution may be determined based on the maximum measurement error tolerance. The maximum measurement error tolerance may be determined at least in part based on user input, and may include a user-indicated confidence level of the measurement as well as a target measurement range (such as a target change in size of a lesion, where the size of lesion is known from the initial scan).

In an example, the at least one scan parameter to be scaled may be selected based on the target contrast to noise ratio and/or target spatial resolution. Additionally or alternatively, a first set of image reconstruction parameters used to reconstruct the one or more images acquired during the initial CT scan may be obtained and one or more reconstruction parameters of the first set of image reconstruction parameters may be scaled based on the target contrast to noise ratio and/or target spatial resolution to generate a second set of image reconstruction parameters, the second set of image reconstruction parameters usable to reconstruct one or more images from data acquired during the first CT scan. The one or more reconstruction parameters may include one or more of a reconstruction kernel, adaptive statistical iterative reconstruction level, slice thickness, pixel size, and reconstructed/displayed field of view.

An example relates to a method for a CT system. The method includes determining a target image parameter for an image to be acquired during a current scan of a patient with the CT system based on a clinical goal of the current scan, obtaining one or more prior scan parameters for a prior image of the patient acquired during a prior scan, and measuring one or more image quality parameters of the prior image. The method further includes adjusting the one or more prior scan parameters to obtain one or more current scan parameters based on the target image parameter, the one or more image quality parameters of the prior image, and a scanning objective, and acquiring projection data usable to reconstruct one or more images of the patient with the CT system by operating the CT system according to the one or more current scan parameters.

The target image parameter may be a target contrast to noise ratio of the image and the clinical goal for the current scan may include a tolerated measurement error for an anatomical feature to be measured in the image, at least in some examples. The one or more prior scan parameters for the prior image may include one or more of an x-ray tube current, an x-ray tube voltage, filter type or shape, imaging resolution mode, and focal spot size used during the prior scan. In an example, the one or more prior scan parameters may be adjusted to achieve the scanning objective while also reaching the target image parameter, and the scanning objective may include lowering a radiation level of the CT system during the current scan or maintaining one or more image quality parameters of the prior image.

In examples, a CT system, such as the CT systems described above, may include a rotatable gantry having a bore centrally disposed therein in which a patient is configured to be positioned, an imaging source positioned within the rotatable gantry and configured to project energy toward the patient, a detector array disposed within the rotatable gantry and configured to receive energy projected by the imaging source and impinged by the patient, and a controller. The controller may be configured to (e.g., store instructions in non-transient memory executable by the controller to) determine a target contrast to noise ratio (CNR) and spatial resolution for an image to be acquired during a current scan of the patient with the CT system based on a clinical goal of the current scan, the clinical goal obtained via user input to the CT system; obtain one or more prior scan parameters for a prior image of the patient acquired during a prior scan; adjust the one or more prior scan parameters to obtain one or more current scan parameters, the one or more prior scan parameters adjusted in order to operate the imaging source with a lowest possible radiation dose while still achieving the target CNR and the target spatial resolution; and acquire projection data via the detector array usable to reconstruct one or more images of the patient with the CT system by operating the imaging source according to the one or more current scan parameters. In an example, the controller may be configured to adjust the one or more measured scan parameters to obtain one or more current scan parameters by adjusting one or more of an x-ray tube current, an x-ray tube voltage, filter type or shape, imaging resolution mode, and focal spot size. In an example, the controller may be configured to adjust one or more image reconstruction parameters used to reconstruct the prior image to obtain one or more current reconstruction parameters in order to operate the imaging source with the lowest possible radiation dose while still achieving the target CNR and the target spatial resolution, and reconstruct one or more images from the acquired projection data using the one or more current reconstruction parameters.

A technical effect of optimizing scan and reconstruction parameters for a current scan based on scan and reconstruction parameters used to generate a prior image of a patient is to reduce patient radiation exposure without compromising the clinical or diagnostic goal of the current scan.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a computed tomography (CT) system, comprising:
    reducing a radiation level of at least one CT scan of one or more successive CT scans performed on a patient based on CT scan information obtained from a previous CT scan performed on the patient, the radiation level reduced relative to a radiation level of the previous CT scan by adjusting one or more parameters of the CT scan information to achieve the reduced radiation level and a target image quality, wherein the target image quality is at most an image quality of the previous CT scan.

2. The method of claim 1, wherein the previous CT scan is an initial CT scan, each of the one or more successive CT scans is performed after the initial CT scan, and each of the one or more successive CT scans is temporally spaced apart from a prior CT scan by a treatment period during which the patient undergoes treatment for a condition monitored by the one or more successive CT scans.

3. The method of claim 2, further comprising performing the initial CT scan with the CT system configured with a first set of scan parameters selected based on an anatomical region of interest being scanned in the initial CT scan.

4. The method of claim 3, wherein the at least one CT scan comprises a first CT scan following the initial CT scan, reducing the radiation level of the first CT scan based on CT scan information obtained from the initial CT scan comprises scaling at least one scan parameter of the first set of scan parameters to generate a second set of scan parameters and performing the first CT scan with the CT system configured with the second set of scan parameters to reduce the radiation level.

5. The method of claim 4, wherein the at least one scan parameter comprises one or more of an x-ray tube current, an x-ray tube voltage, filter type or shape, imaging resolution mode, and focal spot size.

6. The method of claim 4, wherein scaling the at least one scan parameter comprises scaling the at least one scan parameter by an amount based on a target contrast to noise ratio and/or a target spatial resolution for the first CT scan.

7. The method of claim 6, wherein scaling the at least one scan parameter by the amount based on the target contrast to noise ratio and/or the target spatial resolution for the first CT scan comprises scaling the at least one scan parameter by an amount to achieve a lowest possible radiation level while also maintaining a contrast to noise ratio of the first CT scan at or above the target contrast to noise ratio and/or while also maintaining a spatial resolution of the first CT scan at or above the target spatial resolution.

8. The method of claim 6, further comprising determining the target contrast to noise ratio and/or the target spatial resolution based on a clinical goal of the first CT scan and image information taken from one or more images reconstructed from data acquired during the initial CT scan.

9. The method of claim 8, wherein the image information includes information usable to identify a size of a lesion of the patient, wherein the clinical goal comprises measuring the size of the lesion at each of the one or more successive CT scans with a maximum measurement error tolerance, and wherein the target contrast to noise ratio and/or the target spatial resolution are determined based on the maximum measurement error tolerance.

10. The method of claim 8, further comprising selecting the at least one scan parameter to be scaled based on the target contrast to noise ratio and/or the target spatial resolution.

11. The method of claim 8, further comprising obtaining a first set of image reconstruction parameters used to reconstruct the one or more images acquired during the initial CT scan, and scaling one or more reconstruction parameters of the first set of image reconstruction parameters based on the target contrast to noise ratio and/or the target spatial resolution to generate a second set of image reconstruction parameters, the second set of image reconstruction parameters usable to reconstruct one or more images from data acquired during the first CT scan.

12. The method of claim 11, wherein the one or more reconstruction parameters include one or more of a reconstruction kernel, adaptive statistical iterative reconstruction level, slice thickness, pixel size, and reconstructed/displayed field of view.

13. The method of claim 2, wherein reducing the radiation level of the one or more successive CT scans further comprises determining a change in attenuation of the patient relative to the initial CT scan and reducing the radiation level by scaling an x-ray tube current of the CT system during the one or more successive CT scans based on the change in attenuation.

14. A method for a computed tomography (CT) system, comprising:
   determining a target image parameter for an image to be acquired during a current scan of a patient with the CT system based on a clinical goal of the current scan;
   obtaining one or more prior scan parameters for a prior image of the patient acquired during a prior scan;
   measuring one or more image quality parameters of the prior image;
   adjusting the one or more prior scan parameters to obtain one or more current scan parameters based on the target image parameter, the one or more image quality parameters of the prior image, and a scanning objective; and
   acquiring projection data usable to reconstruct one or more images of the patient with the CT system by operating the CT system according to the one or more current scan parameters.

15. The method of claim 14, wherein the target image parameter is a target contrast to noise ratio of the image and wherein the clinical goal for the current scan includes a tolerated measurement error for an anatomical feature to be measured in the image.

16. The method of claim 14, wherein the one or more prior scan parameters for the prior image comprise one or more of an x-ray tube current, an x-ray tube voltage, filter type or shape, imaging resolution mode, and focal spot size used during the prior scan.

17. The method of claim 14, wherein adjusting the one or more prior scan parameters based on the target image parameter and the scanning objective comprises adjusting the one or more prior scan parameters to achieve the scanning objective while also reaching the target image parameter, and wherein the scanning objective comprises lowering a radiation level of the CT system during the current scan or maintaining one or more image quality parameters of the prior image.

18. A computed tomography (CT) system, comprising:
   a rotatable gantry having a bore centrally disposed therein in which a patient is configured to be positioned;
   an imaging source positioned within the rotatable gantry and configured to project energy toward the patient;
   a detector array disposed within the rotatable gantry and configured to receive energy projected by the imaging source and impinged by the patient; and
   a controller configured to:
      determine a target contrast to noise ratio (CNR) and a target spatial resolution for an image to be acquired during a current scan of the patient with the CT system based on a clinical goal of the current scan, the clinical goal obtained via user input to the CT system;
      obtain one or more prior scan parameters for a prior image of the patient acquired during a prior scan;
      adjust the one or more prior scan parameters to obtain one or more current scan parameters, the one or more prior scan parameters adjusted in order to reduce a radiation level of the current scan relative to the one or more prior scans by operating the imaging source with a lowest possible radiation dose while still achieving the target CNR and the target spatial resolution; and
      acquire projection data via the detector array usable to reconstruct one or more images of the patient with the CT system by operating the imaging source according to the one or more current scan parameters.

19. The CT system of claim 18, wherein the controller is configured to adjust the one or more prior scan parameters to obtain the one or more current scan parameters by adjusting one or more of an x-ray tube current, an x-ray tube voltage, filter type or shape, imaging resolution mode, and focal spot size.

20. The CT system of claim 18, wherein the controller is configured to adjust one or more image reconstruction parameters used to reconstruct the prior image to obtain one or more current reconstruction parameters in order to operate the imaging source with the lowest possible radiation dose while still achieving the target CNR and the target spatial resolution, and reconstruct one or more images from the acquired projection data using the one or more current reconstruction parameters.

* * * * *